United States Patent [19]
Baker

[11] Patent Number: 5,307,097
[45] Date of Patent: Apr. 26, 1994

[54] CORNEAL TOPOGRAPHY SYSTEM INCLUDING SINGLE-DIRECTION SHEARING OF HOLOGRAPH GRATING IN ORTHOGONAL DIRECTIONS

[75] Inventor: Philip A. Baker, Orinda, Calif.
[73] Assignee: Kera-Metrics, Inc., Solana Beach, Calif.
[21] Appl. No.: 972,374
[22] Filed: Nov. 5, 1992
[51] Int. Cl.$^5$ .......................... A61B 3/10; A61B 3/00; G01B 9/02
[52] U.S. Cl. .................................. 351/212; 351/221; 351/246; 356/345; 356/353
[58] Field of Search ............... 351/205, 211, 212, 221, 351/245, 246; 364/413.13; 356/353, 359, 354, 347, 348, 345; 359/9, 30, 35

[56] References Cited

U.S. PATENT DOCUMENTS

| | | | |
|---|---|---|---|
| 3,829,219 | 8/1974 | Wyant | 356/354 |
| 3,936,160 | 2/1976 | Von Bieren | 351/205 |
| 4,863,260 | 9/1989 | Gersten et al. | 351/246 |
| 5,062,702 | 11/1991 | Bille | 351/212 |

OTHER PUBLICATIONS

Rimmer, et al. "Evaluation of Large Aberrations Using a Lateral-Shear Interferometer Having Variable Shear" *Applied Optics*, vol. 14, No. 1, Jan. 1975.

*Primary Examiner*—Bruce Y. Arnold
*Assistant Examiner*—John Juba, Jr.
*Attorney, Agent, or Firm*—Cahill, Sutton & Thomas

[57] ABSTRACT

A system for producing a three-dimensional image of a surface, such as a surface of a cornea, includes a laser beam that passes through a beamsplitter and an objective lens to produce a spherical wavefront that impinges on the cornea and is reflected by the cornea as a return beam back through the objective lens. The return beam is reflected by the beamsplitter through an imaging lens that focuses the return beam onto an imaging screen, through a dual phase plate, and onto a photosensitive array. The dual phase plate includes two sets of spaced periodic refractive features spaced along orthogonal directions. The phase plate is modulated by incrementing it at a 45 degree angle relative to the first and second directions, thereby simultaneously producing phase shear along the two orthogonal directions. The resulting intensities at each pixel of a CCD camera are digitized and used to compute an optical phase difference (OPD) map consisting of the relative deviation of the cornea surface from the impinging spherical wavefront at each pixel. The OPD map then is summed with a "spherical map" of the impinging spherical wavefront, which has height coordinates measured relative to a limbus plane under the cornea, to obtain a complete three-dimensional image of the cornea. Various d-spacings of the dual phase plate patterns, in conjunction with corresponding capture intervals or shifts produced by the incrementing, allow scaling of the sensitivity of the system to allow "close up" viewing of the cornea.

15 Claims, 3 Drawing Sheets

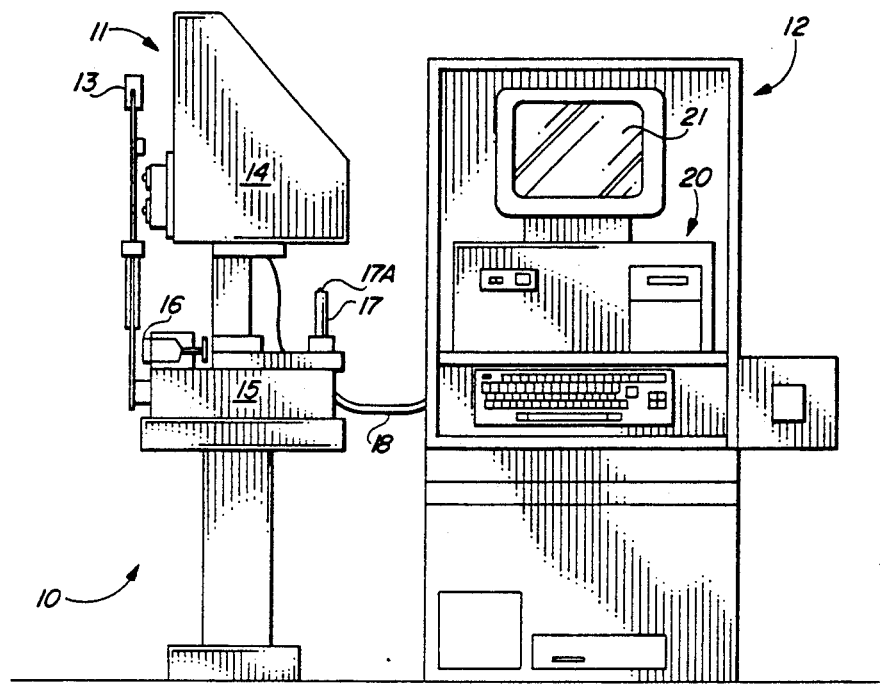
FIG. 1
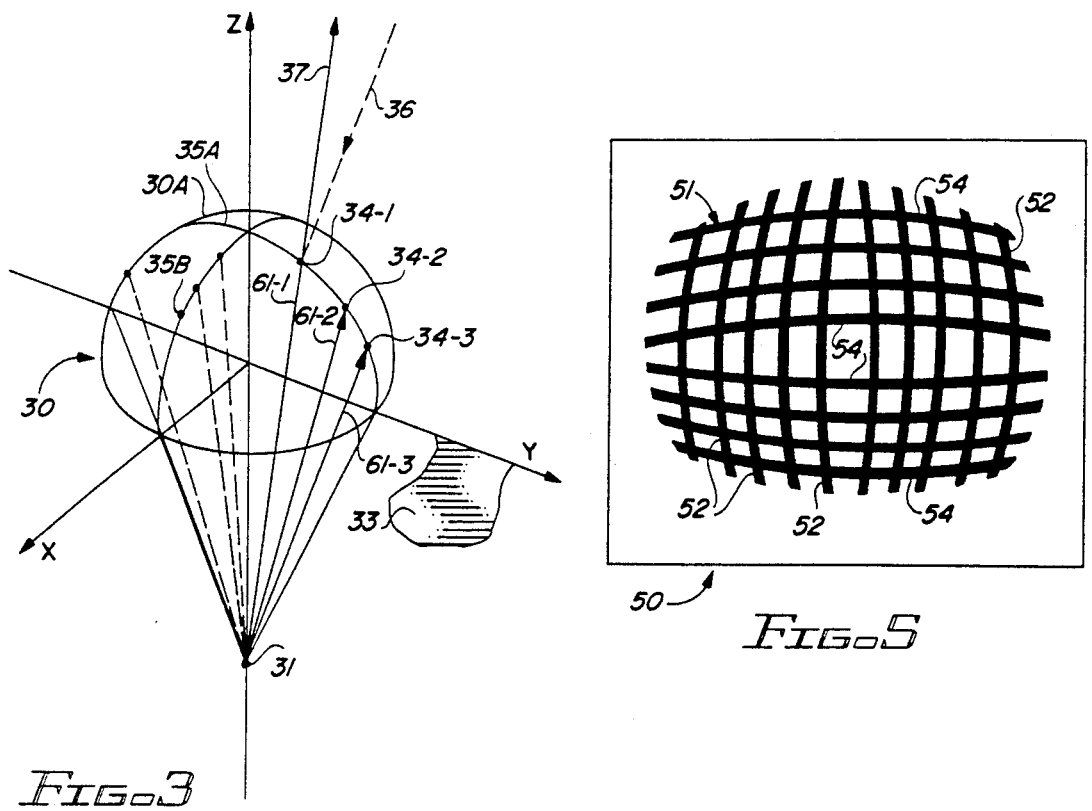
FIG. 3
FIG. 5

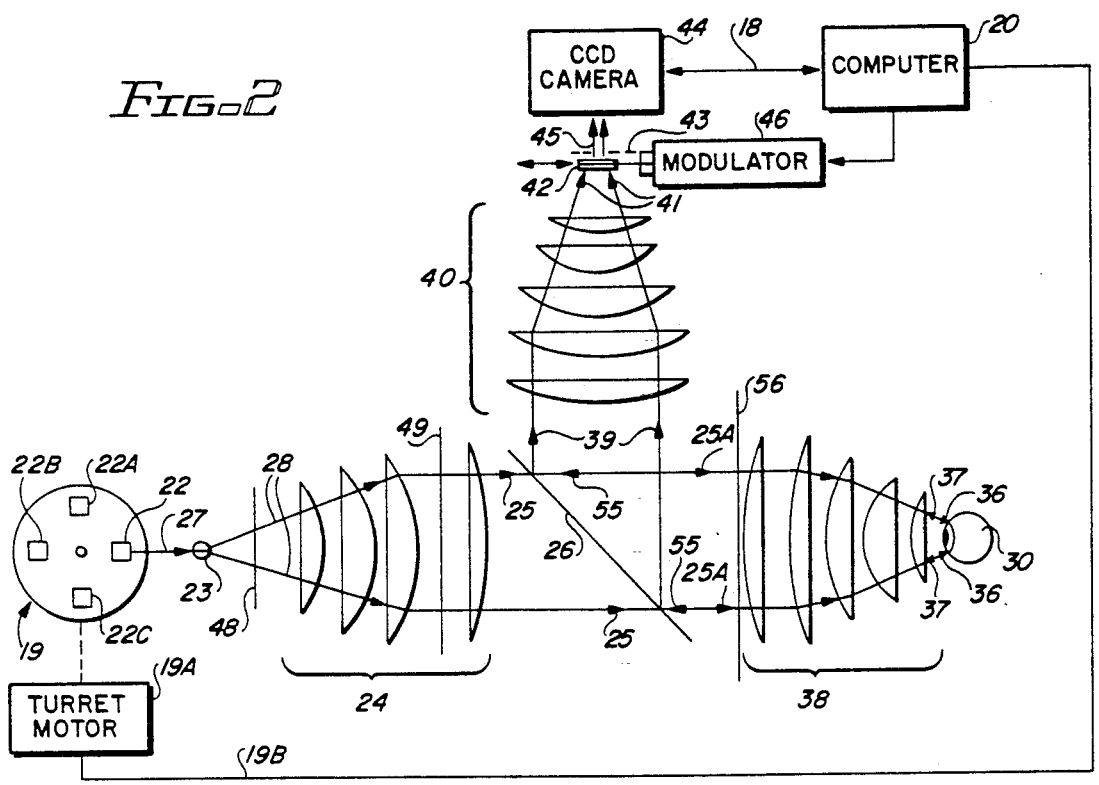
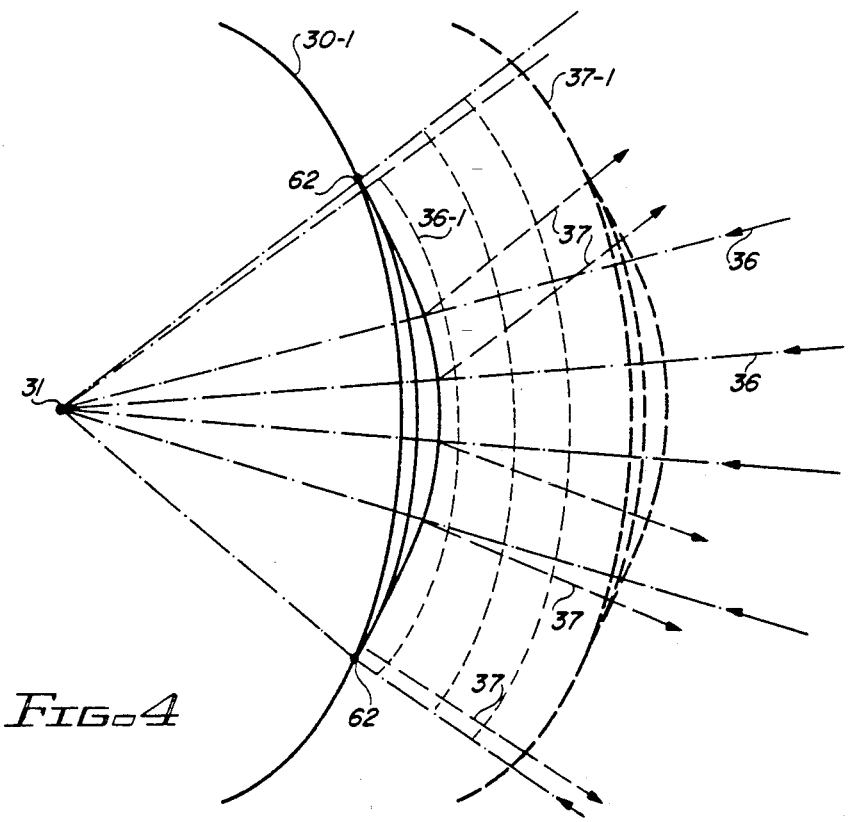

CORNEAL TOPOGRAPHY SYSTEM INCLUDING SINGLE-DIRECTION SHEARING OF HOLOGRAPH GRATING IN ORTHOGONAL DIRECTIONS

BACKGROUND OF THE INVENTION

The invention relates to a device and technique for measuring the topography of a cornea, and more specifically to single-direction incremental displacement or modulation of a cross grating pattern on a phase plate to obtain simultaneous phase shearing in orthogonal x and y directions, imaging the resulting composite diffraction pattern, and operating on the resulting data to compute the height of each pixel of the cornea and store and display a three-dimensional image thereof.

Various corneal topography measurement devices are available. For example, a commonly used TOMEY automatic keratoscope includes an automatic ring detection algorithm and produces a "power" or diopter map, rather than a topographic map of the cornea. (A diopter is the inverse of the radius of curvature in meters.) Eyses Corporation, of Houston, Tex. makes a simplified video keratoscope which operates on the same principles as the TOMEY device, measuring distortion of projected illumination rings by the cornea to extract slope information that is converted to a diopter map. Both of the devices have the disadvantages that the "maps" produced do not cover the full cornea, and furthermore they fail to actually measure the center region of the cornea, at which accurate measurements are most critical. The "shadows" of the rings contain distortion by non-spherical features of the cornea, but are difficult to digitize over the range of the cornea, especially in the central areas. Lateral resolution of points of the points of the diopter maps are not as accurate as desirable. The present assignee has developed an experimental fringe interpretation cornea topography measurement device in which a return beam reflected by the cornea is split, and phase shearing operations are separately performed in the x and y directions. The results are separately imaged by a photosensitive array and the resulting data then is used to compute the relative phase and the relative height of the cornea at each pixel. This technique has the main disadvantage that it is much slower than desired, and is subject to inherent mechanical inaccuracies involved in shifting the x and y phase plates in separate operations.

There currently is an unmet need for an improved automatic keratoscope which provides an accurate topography of the full cornea, especially the center portions. There is an unmet need for accurately producing a true topography map, rather than the conventional "power" maps or diopter change maps of the cornea.

SUMMARY OF THE INVENTION

Accordingly, it is an object of the invention to provide an improved system and technique for precisely digitizing an anterior surface of a cornea.

It is another object of the invention to provide a system which can measure changes in the tear film interface and or changes in the cornea surface as a result of contact lens thereon. It is another object of the invention to provide a system that can measure changes in the anterior and posterior surfaces of the cornea as a result of a contact lens.

It is another object of the invention to more rapidly and more precisely measure and digitize the topography of a cornea than has been practical with prior devices.

It is another object of the invention to provide an improved system and technique for digitizing an interior surface of an eye.

It is another object of the invention to provide an improved technique for more precisely mapping both horizontal and vertical features of the cornea than has been accomplished by the prior art.

Briefly described, and in accordance with one embodiment thereof, the invention provides a system and technique for producing a three-dimensional image of a surface, such as a surface of a cornea, in which a laser beam, after being passed through a beamsplitter and an objective lens to produce a spherical wavefront that impinges on the cornea, is reflected by the cornea as a return beam back through the objective lens. The impinging wavefront has a radius of curvature of a typical cornea. The return beam is reflected by the beamsplitter through an imaging lens that focuses the return beam onto an imaging screen, through a dual phase plate, and onto a photosensitive array. In accordance with the present invention, the dual phase plate includes two sets of spaced periodic refractive features, such as grating lines or periodic variations in thickness or density spaced along orthogonal directions. The phase plate is modulated by incrementing it at a 45 degree angle relative to the first and second directions, thereby simultaneously producing phase shear along the two orthogonal directions. Composite orthogonal fringes representing deviation of the cornea from the impinging spherical wavefront are imaged onto the photosensitive array. The resulting intensities at each of the pixels are digitized and stored. The digitized intensity data then is used to compute an optical phase difference (OPD) map consisting of the relative deviation of the cornea surface from the impinging spherical wavefront at each pixel. The OPD map then is summed with a "spherical map" of the impinging spherical wavefront, which has height coordinates measured relative to a limbus plane under the cornea, to obtain a complete holographic image of the cornea. In accordance with the invention, various lasers of different wavelengths are used to allow imaging and profiling of various interior surfaces of the eye and to allow analysis of material properties of the eye. Various d-spacings of the dual phase plate x and y patterns, in conjunction with corresponding image capture intervals or shifts produced by the incrementing, allow scaling of the sensitivity of the system to allow "close up" viewing of smaller areas of the cornea.

BRIEF DESCRIPTION OF THE DRAWINGS

FIG. 1 is a diagram of a corneal topography system of the present invention.

FIG. 2 is a diagram illustrating the optical portion of the system of FIG. 1.

FIG. 3 is a perspective diagram illustrating light rays impinging upon and reflected from a cornea.

FIG. 4 is a diagram use in describing the operation of the system shown in FIGS. 1 and 2.

FIG. 5 is a diagram illustrating a display produced in response to fringe images received by the camera of FIG. 2.

DETAILED DESCRIPTION OF THE PREFERRED EMBODIMENTS

Figure 7:
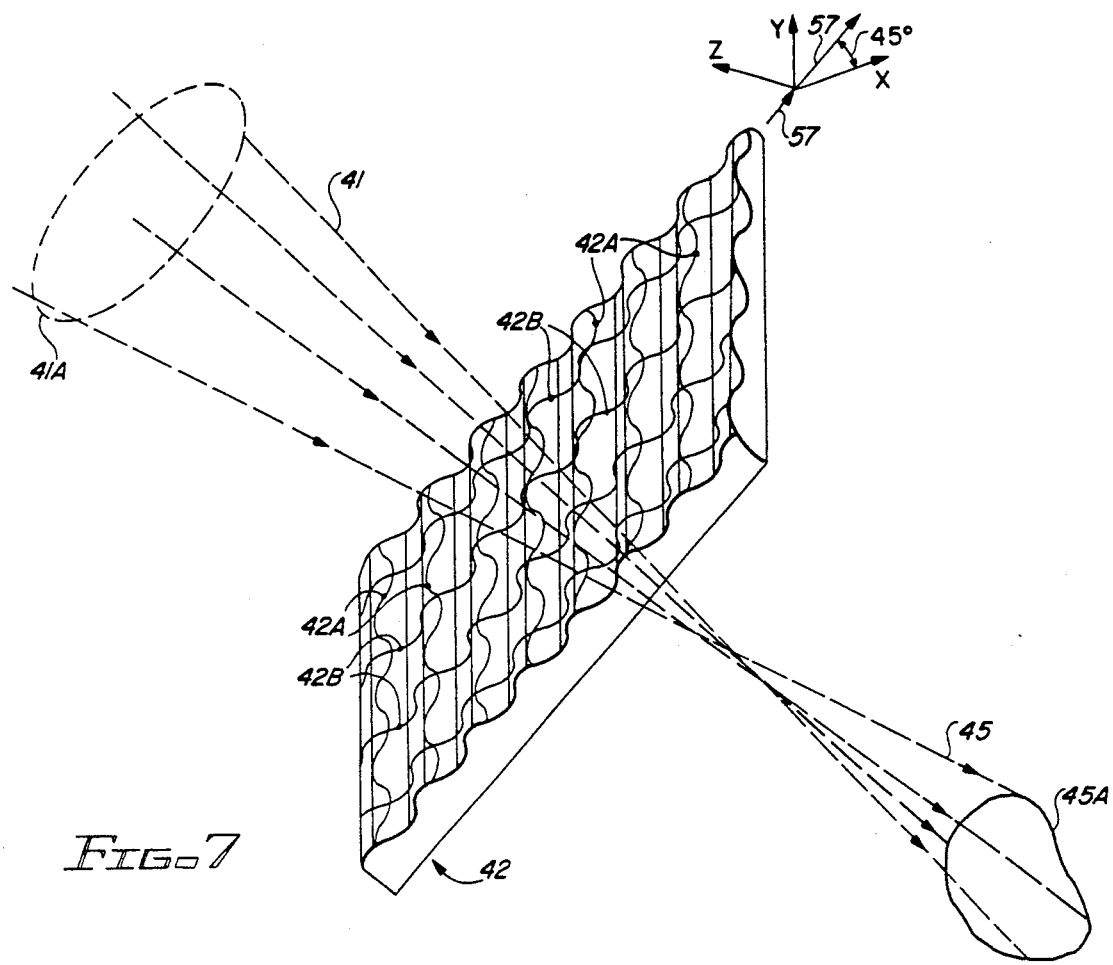
FIG. 7 is an isometric view illustrating modulation of a "composite" cross-sinusoidal dual phase plate to simultaneously produce cross phase shear in orthogonal directions.

Referring to FIGS. 1 and 2, topographic system 10 includes a data acquisition system 11 that includes an optical system 14 supported on a X-Y table 15. The position of table 15 can be manipulated by means of a joystick 17. A digital indicator 16 provides an readout 3 of the position of the optical system 14 relative to a stationary chin rest 13 that properly positions the eye of the patient. Optical system 14 includes the elements shown in FIG. 2, and sends digitized interference fringe information over a cable 18 to an RS232 port of a computer system 12, which preferably,, includes an 486-based IBM compatible computer 20 and a VGA monitor 21. A separate real time monitor also can be connected to the optical system 14, if desired.

Joystick 17 is manipulated to align optical system 14 with the cornea of a patient whose chin is properly supported by rest 13. Button 17A on joystick 17 is depressed by the operator to "acquire" or "capture" image "frames" after the optical system 14 has been properly aligned to the cornea.

Referring to FIG. 2, optical system 14 includes a narrow band diode laser 22. Diode laser source 22 can be a turreted laser structure providing multiple frequency beams. Preferably, both visible and infrared laser diodes can be utilized, the infrared and near-infrared wavelengths being more suitable for maximum interface reflection at the posterior surface of the cornea and also for imaging retinal surfaces. As indicated in FIG. 2, lasers 22A, 22B ahd 22C are supported on a turret 19, which can be rotated so as to align laser 22, 22A, 22B, and 22C into spherical lens 23.

Each of lasers 22, 22A, 22B and 22C emits light of a different wavelength. Turret 19 can be controlled by an advancing mechanism 19A in response to signal 19B produced by computer 20, if desired. For example, if laser 22A is an infrared laser, and the objective lens system 38 focuses it onto the retina of eye 30, rather than onto the interior of the cornea, then the retina can be imaged. The cornea, lens, and other media in the eye are transparent to infrared light, so the reflections from the retina, when imaged onto the camera and processed, can provide information about the materials and the other interfaces of the eye, including the retinal surface, the lens of the eye, and the back or posterior surface of the cornea. The availability of different wavelength light from the various lasers on turret 19 allows optimization of the imaging of the various interface surfaces within the eye.

Whichever laser is aligned with spherical lens 23 produces a beam 27 that passes through a spherical lens 23 to produce diverging rays 28. Diverging ball lens 23 is a simple spherical graded index ball lens which is used to shape the input diode laser beam 27 for multiple wavelengths, reducing chromatic aberration and spherical aberration and also reducing astigmatic features of the diode laser output.

Diverging rays 28 pass through apodizer 48 and a collimating lens system 24, producing a collimated beam 25 that passes through a beamsplitter 26. Apodizer 48 constitutes an axicon and/or thin film apodizer to homogenize and mix the source wavefront so as to produce uniform illuminance. Collimating lens system 24 consists of a suitable number of converging lens arrayed to shape the output beam of diode laser 22 for multiple light wavelengths, to provide minimum aberration of the wavefront shape. (The term "lens system" as used herein encompasses one or more individual lens elements co-acting to focus or otherwise shape a light beam or wavefront.) Beam splitter 26 is a 45 degree, 60 percent transmissive, 40 percent reflective polarized plate beam splitter with anti-reflective coating on the left surface. Fixation reticle target 56 provides central fixation for the patient and operator during alignment and exposure. The reticle pattern is matched to a centration reticle in order to provide focusing and centering information during acquisition of the corneal image.

Part 25A of beam 25 is transmitted through objective lens system 38 to produce a spherical wavefront 36 that has a radius of curvature approximately equal to that of a typical cornea 30. The dimensions of laser beam 25A (typically 3 inches) and the numerical aperture and F ratio of objective lens system 38 (e.g., 0.754 and 0.600, respectively) are such that the anterior surface of an average cornea 30, which is 12 millimeters in diameter, is covered by the converging spherical wavefront 36.

Objective lens system 38 covers an area 12 millimeters in diameter for a cornea having a normal 8 millimeter radius of curvature. The range of acceptable perturbations from the corneal anterior surface is 20 diopters of deviation from an average measured sphere having an 8 millimeter radius of curvature. The aperture of the illuminated area increases for larger corneal radius of curvature and decreases for smaller corneal radius of curvature. Both the anterior surface and the interior surface of the cornea can be measured and/or imaged for topographic and refractive analysis.

A reflected return beam designated by arrows 37 is reflected by cornea 30, collimated by lens system 38, impinges on the left surface of beam splitter 26, and is reflected as beam 39 into imaging lens system 40. Imaging lens system 40 consists of a lens design including five or six diverging lens of decreasing radius of curvature and is identical to and matched with objective lens system 38 to within 1/10 of a wavelength, to suppress geometric distortion and maintain a telocentric transfer of the object (i.e. the cornea 30) to the image plane for a three-dimensional wavefront shape. The resulting return image beam 41 impinges on phase plate 42.

Phase plate 42 is scanned or shifted across the return image beam 41, creating slope fringes that contain all of the phase contour information from cornea 30. A modulator 46 incrementally shifts phase plate 42 in its plane at an angle of 45 degrees relative to the orthogonal x and y directions, simultaneously producing phase shear in the x and y directions. In accordance with the present invention, this overcomes many of the problems of the prior art. (In the prior art, the phases of separate x and y single phase plates are sheared in separate shearing operations in separate directions. The images are separately digitized and processed in separate operations, and are integrated as separate x and y phase maps. The slowness and inaccuracy associated with such operations are avoided by the present invention.)

The "shadow" image 45 resulting from the shearing is produced on viewing screen 43. Viewing screen 43 preferably is constructed of light scattering material that diffuses the input light and acts as a back-lit screen to achieve optimal stray light suppression. The image on viewing screen 43 is detected by CCD camera 44.

CCD camera 44 includes a CCD photosensitive array (or other suitable photosensitive array) and electronic circuitry that converts resulting analog signals produced for each pixel into corresponding digital signals. Preferably, CCD camera 44 includes a 512 pixel by 480 pixel array which is automatically scanned in a "frame-grabbing" operation. The scanned analog signals are digitized to produce complete interference fringe information for each pixel of the photosensitive array (i.e., for each pixel of the entire image), and outputs that digital data via cable 18 (FIG. 1) to computer 20 in order to effectuate capturing of one or more frames of image data in response to depressing of joystick button 17A.

FIG. 5 illustrates the interference fringe image which is "seen" by camera 44 and digitized in the course of a single translation of x pattern 42A and y pattern 42B of dual phase plate 42 across return image beam 41 and then captured or "grabbed" as a single "frame" of data. More specifically, reference numeral 51 illustrates a composite image of both the vertical fringes 52 and the horizontal fringes 54 simultaneously produced by phase shearing in the x and y directions.

In operation of the system 10 of FIG. 1, the patient is aligned so that the chin rest 13 maintains the patient's eye as level and stable as possible with respect to the plane of the objective lens 38. The light emerging from lens 38 is focused down to a fine point, so that it is positioned at the geometric center of the cornea 30. When the objective lens system 38 is positioned so that the fine point or focal spot is reflected back along the same path as the impinging rays, it is centered on the cornea; the center of the cornea is the only portion which can cause the reflected focal spot rays to return as a collimated beam to the beamsplitter 26 and from there to imaging lens system 40.

The digitized image of the focal spot of the cornea actually represents the optical system error, because the focal spot is so small in diameter (roughly a micron) that the error across it is essentially zero. Consequently, any irregularities in the holographic image of the focal spot on the cornea represent optical system errors. The foregoing technique allows proper location of the patient's cornea with respect to the system optics with a high degree of reliability, and also provides an indication of optical system error which can be used to correct data subsequently obtained for optical system errors.

The light at the focal spot will be reflected back through the optical system when the spot is as small as possible and is located at the geometric center of the cornea. An image of the focal spot will show on the monitor 21 and/or on a real time monitor, if one is being used. At that point, the operator depresses the joystick control button 17A and captures that z location. The joystick then is operated to move the optical system 14 closer to the patient's eye, keeping the cornea image aligned on the screen of monitor 21 so that when the cone of light coming from lens 38 has reached a point that it fits the eye's limbus, the screen of monitor 21 will be filled with the interference pattern shown in FIG. 5, with the number of fringes minimized to produce a null pattern, in which the fringe lines 52 and 54 are distorted from being straight lines in accordance with the various non-spheric aspects of the cornea relative to the impinging spherical wavefront 36. For example, if the cornea shape is perfectly spherical, the output pattern will show one fringe.

It should be understood that the manner in which the base radius curvature is obtained requires that the above-mentioned movements of optic system 14 start from a "null" phase pattern or fringe pattern displayed on monitor 21 and progress to a different null fringe pattern to accurately measure a radius of curvature that accurately best fits the spherical impinging wavefront 36 produced by objective lens system 38. The base radius of curvature then can be modified to eliminate the effects of "defocus" error. The defocus error is the amount of residual linear wavefront misfit between the cornea and the impinging wavefront. That is, the defocus error can be determined, and it's effect can be easily subtracted from the base radius of curvature.

When the optical system 14 has been moved so that the above-mentioned cone of light fits the corneal surface, the distance the optical system 14 has moved is equal to the average radius of curvature of the cornea, and hence, of the impinging wavefront 36. This distance therefore is determined from the two z locations captured by the operator in the above-mentioned depressing of joystick button 17A.

Corneal phase contours 52 and 53 of FIG. 5, which have been digitized by the time they are displayed on monitor 21, are stored in corresponding files, the contents of which are used with well known equations to compute the behavior of the light reflected from the cornea in physical terms, including the x slope, y slope, and surface OPD curvature at each pixel. For example, see the publication "Optical Shop Testing", first edition, 1978, by Daniel Malacara, published by John Wiley and Sons, incorporated herein by reference. Especially see chapters 4 and 9 of this reference. Also see "Wave-front Estimation from Wave-front Slope Measurements", by W. H. Southwell, in the Journal of the Optical Society of America, volume 70, No. 8, August, 1980, incorporated herein by reference.

In the system described, phase contours 52 and 53 of FIG. 5 are positioned to within 1 pixel, which means that the x,y coordinates of each pixel are accurate to within 10 microns. A bend or change in a fringe that causes a deviation of one optical fringe spacing corresponds to a change of the cornea surface height (in the z direction) of 72 microns for that pixel. This amount is determined by the wavelength of light produced by laser 22. Amounts of astigmatism and asphericity of the corneal surface can be quantified from this information. If radial keratotomy incisions have been made in the cornea, the locations of the incisions and their affect can be precisely determined.

Perhaps the manner in which the data is processed by computer 20 can be understood better by understanding the light paths in the structure shown in FIGS. 3 and 4. In FIG. 3, an imaginary flat "limbus plane" 33 is defined by the x and y axes through which limbus plane 30A passes. Arcs 35A and 35B in FIG. 3 represent the intersection of the x-z and y-z planes with the anterior surface of the cornea. Imaginary horizontal planes passing through points 34-1, 34-2, and 34-3 etc. represent different elevations measured with respect to the limbus plane 33. This is shown to illustrate the point that all values of z, that is, the elevation of each point on the anterior surface of cornea 30, are measured relative to limbus plane 33. The curvature of each wavefront 36 impinging from objective lens system 38 onto cornea 30 is spherical, and the z coordinate of each point of the anterior surface of cornea 30 represents the deviation of that point of the cornea surface from spherical wavefront 36. For example, if the cornea surface were perfectly spherical (or of any other precisely understood and quantified shape), so as to match the curvature of the incoming wavefront 36-1 (FIG. 4), the computed value of z would be zero. It should be appreciated that the impinging wavefront 36 could be altered to be other than spherical to create a different initial condition with respect to which the cornea shape differences are measured. The computations constructing the OPD map then are computed and superimposed onto the coordinates of the impinging waveform.

The continuous rays of light 37 are reflected, as if they come from a virtual focal point 31, from the cornea back through lens system 38 as a return beam. Each ray of light is reflected back at a slope that represents the deviation of that point from impinging spherical wavefront 36. The reflected return wavefront 37, which carries with it information on the shape of the cornea, passes back through the optical system to the plane of holographic phase plate 42. That light is sheared by the dual phase plate 41 to produce the phase contours 52,54 of FIG. 5.

After the "local deviation" or relative height of the elevation of each pixel is analyzed and a reconstructed cornea surface has been computed to produce a OPD topographic map, those local deviations are summed with the coordinates of the spherical impinging wavefront 36, to superimpose the "OPD map" onto the spherical shape of impinging wavefront 36 to obtain the precise coordinates of the cornea surface relative to limbus plane 33A.

It should be understood that the z deviations, collectively referred to as the OPD (optical phase difference), are what is computed by the above mentioned well known techniques. A "sagittal" profile of the cornea is then constructed in three dimensions on all meridians across the cornea from the OPD map information. This is done by means of a simple algorithm executed by computer 20 which takes the z values from the OPD map at each pixel location and computes the local radius of curvature using that information and the previously obtained base radius of curvatures to compute radii such as 62-1, 62-2, 62-3 etc. From that information a three-dimensional profile of the cornea is computed.

The sensitivity of the system shown in FIGS. 1 and 2 is a function of the wavelength of the light 27 produced by laser 22 and the way that the three-dimensional image is formed. The sensitivity can be varied by changing the holographic structure to allow more wavefront shear or less wavefront shear at the return beam focal position. This can be accomplished by changing the holographic pattern to introduce a higher or lower sensitivity scale (i.e., providing a lesser or greater d-spacing of the holographic pattern). The present embodiment of the invention has a mid-range sensitivity scale that can measure changes in the elevation of the surface of the cornea with resolution low as 0.1 microns and up to 2000 microns. Such scaling or adjusting of the sensitivity of the optical system 14 permits analyzing very complex phase patterns. Consequently, for high sensitivity, the appearance of the post-operative corneal surface can produce a highly aberrated fringe pattern that will much more accurately measure the depths and shapes of incisions and the features of sutures than if the mid-range sensitivity holographic plate is being used. It should be understood that the higher the sensitivity, the lower the dynamic range or effective area of the cornea that can be accurately profiled. This capability can allow a physician to carefully monitor conditions in the patient's cornea after, for example, making an arcuate incision much more closely than is possible at a lower sensitivity.

Thus, in accordance with the present invention, the scalable sensitivity options permit additional viewing of a wide range of corneal features with high resolution.

Figure 6:
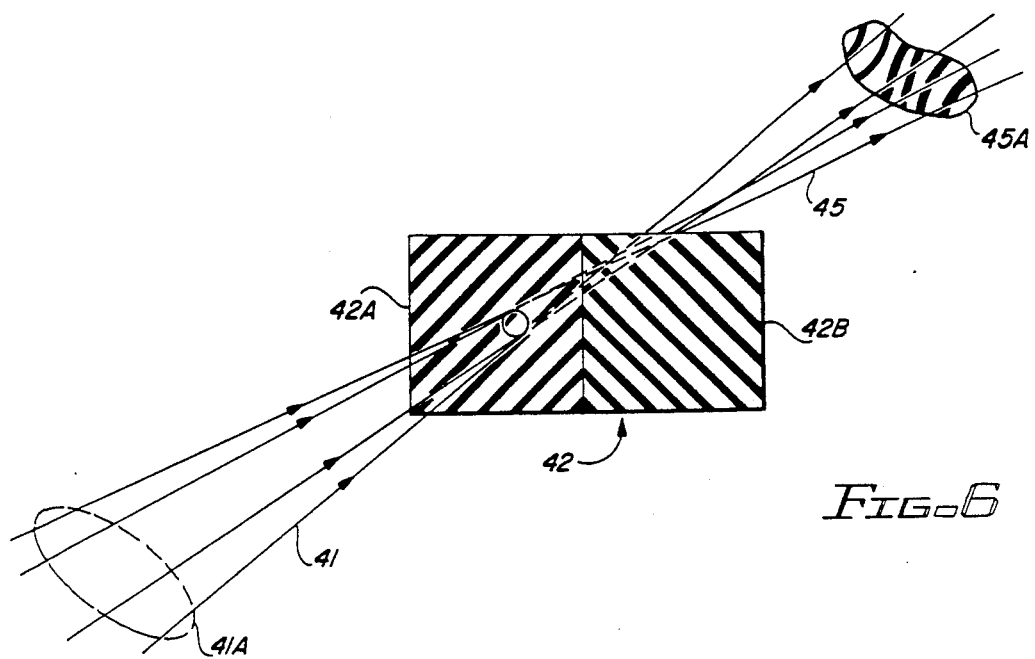
FIG. 6 is an isometric view illustrating modulation of a cross-sinusoidal hologram dual phase plate to simultaneously produce cross phase shear in orthogonal directions to produce a 360 degree phase pattern.

In FIG. 6, dual phase plate 42 contains side-by-side sinusoidal transmissive (or reflective) grating patterns in the x and y directions, respectively. Numeral 42A indicates, by way of example, opacity-to-transparency sinusoidal thickness variations of plate 42 in the x direction, and numeral 42B indicates such thickness variations in the y direction. Numeral 41 designates light emerging from image lens system 40 and impinging on dual phase plate 42. Dotted line 41A represents the return image, and numeral 45A represents the "sheared image" phase pattern produced by the effect of the modulation of holographic grating 42 on the impinging "unsheared" corneal image 41.

In accordance with an important aspect of the invention, dual phase plate 42 is modulated by shifting it in the plane of the x and y directions at an angle of 45 degrees between them in the direction of arrow 42, "simultaneously" producing phase shear in both the x and y directions in a single operation.

Modulation stage 46 includes a linear actuator and a motor controller (not shown) that operates a feedback loop to move phase plate 42 in a continuous manner related to the wavelength of laser beam 27. Phase plate 42 is controlled over it's full travel to within a small fraction of the operating wavelength of laser 22. The resulting phase-shifted "shadow" images impinging on CCD camera 44 then are "acquired" at selected intervals over the stepped travel extent of phase plate 42 in direction 42A of FIG. 6, to provide simultaneous phase shear in both the x and y directions, causing superposition of horizontal fringes 52 and vertical fringes 54 as shown in FIG. 5. This intensity data of the digitized images then is used, pixel-by-pixel, with the above-mentioned well known equations, to compute the final three-dimensional image of the cornea (or other target being profiled) as a function of the slope changes across the full aperture of the illuminated object.

In FIG. 7, "composite" dual phase plate 42 contains coextensive overlapping or superimposed sinusoidal transmissive grating patterns in both the x and y directions, as shown. Numeral 42A indicates opacity-to-transparency sinusoidal thickness variations of plate 42 in the x direction, and numeral 42B indicates such thickness variations in the y direction. Numeral 41 designates light emerging from image lens system 40, as described with reference to FIG. 6. Numerals 45 and 45A represent the sheared image phase pattern produced by the "modulating" of holographic grating 42 on the impinging "unsheared" corneal image 41, 41A. This embodiment of the invention avoids errors due to possible "built in" 3-direction mechanical differences between the x and y portions of the scan of the side-by-side dual phase plate shown in FIG. 6. Furthermore, this embodiment of the invention requires only half as many "frame grabbing" operations as for the embodiment of FIG. 6, and should result in higher speed, more accurate operation.

It should be understood that the translation of dual phase plate 42 in the direction of arrow 57, at an angle of 45 degrees to both the x grid pattern 42A and the orthogonal y grid pattern 42B can be continuous, rather then stepped at half-wavelength intervals. For continuous movement of dual phase plate 42, the "frame grabbing" of the sheared images detected by CCD camera 44 must be synchronized with the continuous movement of dual phase plate 42 so as to capture sheared images at half-wavelength intervals of the dual phase plate travel. Software executed by computer 20 to control the movement of modulator 46 and the frame grabbing operation effectuates this synchronization. The result of such continuous movement modulation is to increase the speed of producing the topography of the cornea (or performing other characterizations of the eye).

Thus, in accordance with the present invention, a suitable actuator system, such as a piezoelectric actuator, modulates a transmissive or reflective dual phase plate that perturbs the collected light in a prescribed manner relative to the surface shape of the cornea or other target and the effect of the return wavefront on the phase shape is imaged onto CCD camera 44. The movement of the modulation stage 46 can be controlled by a stepper motor, piezoelectric actuator, DC controlled analog feedback system, magnetically assisted drive system, or the like.

In accordance with another aspect of the present invention, the modulation stage 46 has a variable control function to allow multiple wavelength system operation, in conjunction with the multiple wavelength laser source, such as a turreted support that indexes lasers of various wavelengths into spherical lens 23, in conjunction with different modes of operation of modulation stage 46. As mentioned above, the material of the eye is transparent to certain infrared or near-infrared wavelengths, so a laser producing a suitable wavelength can be selected, in conjunction with a corresponding dual phase plate 42 and an appropriate modulation thereof, to allow profiling of the effect of contact lenses on the shape of the cornea. Or, reflection of a spot focused on the retina, using a wavelength of about 880 to 940 nanometers, can be used to analyze other interior features or material properties of the eye. For example, changes in refractive index, retinal cell count analysis and the like can be accomplished.

Dual phase plate 42 can be implemented in a variety of ways. It can be a transmissive grating or phase plate constructed by mechanical means, chemical etching, photographically assisted etching, holographic exposure in thermoplastic, liquid crystal, or magnetoptical materials. Or, it can be a reflectance grating formed holographically, mechanically, chemically, by vapor deposition, photographically, etc. Also, "graded index" gratings or sinusoidal phase plates can be formed using ion implantation or co-polymer processes in glass or plastic materials.

The above described implementation of the invention allows rapid analysis of very high resolution images. The sensitivity can be adjusted to obtain height information to within 0.01 diopters and to position x,y coordinates to within 6 to 10 microns for any spot on the cornea.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A method of producing a three-dimensional image of a surface, comprising the steps of:
   (a) producing a beam of light of a first wavelength, passing the light through a diverging lens collimating light from the diverging lens by means of a collimating lens passing light from the collimating lens through a beam splitter and passing light from the beam splitter through an objective lens to produce a wavefront that impinges on the surface and is reflected thereby;
   (b) collimating light reflected from the surface by means of the objective lens and reflecting that collimated light by means of the beam splitter into an imaging lens;
   (c) passing light emanating from the imaging lens through a dual phase plate having first and second periodic diffracting features repeated along first and second directions, respectively;
   (d) during step (c), modulating the position of the dual phase plate in a third direction to simultaneously produce phase shearing in the first and second directions to produce superimposed first and second phase patterns emanating from the dual phase plate;
   (e) sensing the superimposed first and second phase patterns by means of an array of photosensitive elements;
   (f) digitizing signals produced by the array in response to the first and second phase patterns for each pixel of the array; and
   (g) operating on the digitized signals to compute the relative height of each pixel of the surface.

2. The method of claim 1 wherein the surface is a cornea of an eye, and the wavefront produced by the objective lens and impinging on the cornea is a spherical wavefront, the relative heights of the surface constituting an optical phase difference (OPD) representing deviations of the height of the cornea at each pixel from the height of the spherical wavefront impinging on the cornea at that pixel, the method including superimposing the relative heights constituting the OPD map onto relative heights of the spherical wavefront relative to a reference plane to obtain an accurate coordinate map of the cornea.

3. The method of claim 2 wherein the first and second directions are orthogonal x and y directions in a plane of the dual phase plate, and wherein the third direction is in the plane of the dual phase plate and is oriented 45 degrees relative to the x and y directions.

4. The method of claim 3 wherein the modulating includes incrementing movement of the phase plate in increments of one half of the first wavelength.

5. The method of claim 4 including displaying the coordinate map of the cornea on a CRT screen.

6. The method of claim 4 including providing light of a second wavelength which is shorter than the first wavelength and performing steps (a) through (g) for that light, and incrementing movement of the phase plate in accordance with the second wavelength to characterize interior properties of the eye.

7. The method of claim 6 where a portion of the cornea includes an incision and a suture.

8. The method of claim 2 including computing the radius of curvature at pixels of the coordinate map, and converting the radii of curvature to diopter units.

9. A device for producing a three-dimensional image of a surface, comprising in combination:
   (a) a laser providing a first beam having a first wavelength;
   (b) a first lens through which the first beam passes, the first lens diverging the first beam;
   (c) a second lens collimating the first beam to produce a second beam;
   (d) a beam splitter through which a portion of the second beam passes;
   (e) a third lens through which the portion of the second beam passes, the third lens focusing the portion of the second beam onto the surface, the surface reflecting a fourth beam back through the third lens to produce a fifth beam which is reflected by the beamsplitter to produce a sixth beam;
   (f) a dual phase plate having first and second periodic diffracting features along first and second directions, respectively, in a plane of the dual phase plate;
   (g) a fourth lens through which the sixth beam passes to produce a seventh beam which diverges and passes through the dual phase plate;
   (h) a modulator coupled to the dual phase plate and shifting the dual phase plate in a third direction to simultaneously shear the phase of the seventh beam in both the first and second directions, producing an eighth beam containing phase shear in the first and second directions;
   (i) an array of photosensitive detector elements receiving the eighth beam and means for digitizing light intensity signals produced by the array at each pixel of the image represented by the light intensity signals; and
   (j) means for computing the relative height of each pixel of the surface from the digitized light intensity signals.

10. The device of claim 9 including a second laser, and means for orienting the second laser to produce the first beam with a second wavelength which is shorter than the first wavelength.

11. The device of claim 9 wherein the second wavelength has a value to which interior portions of the eye are substantially transparent.

12. The device of claim 11 including means for adjusting amounts of incremental shifting of the dual phase plate by the modulator according to the wavelength of the first beam.

13. The device of claim 9 wherein the dual phase plate includes periodic thickness variations in the x and y directions, having an amplitude of one half the wavelength of the laser light, and a period equal to an integral number of half wavelengths of the laser light.

14. The device of claim 9 wherein the dual phase plate includes rectangular periodic opaque grid sections spaced along the x and y directions with a period equal to an integral number of half wavelengths of the laser light.

15. A method of producing a three-dimensional image of a surface, comprising the steps of:
   (a) producing light of a first wavelength, passing the light through a diverging lens collimating light from the diverging lens by means of a collimating lens, passing light from the collimating lens through a beam splitter producing a wavefront that impinges on the surface and is reflected thereby;
   (b) reflecting light returned from the surface by means of the beamsplitter and causing that light to pass into a dual phase plate having first and second periodic diffracting features repeated along first and second directions, respectively;
   (c) during step (b), modulating the position of the dual phase plate in a third direction to simultaneously produce phase shearing in the first and second directions to produce superimposed first and second phase patterns emanating from the dual phase plate;
   (d) sensing the superimposed first and second phase patterns by means of an array of photosensitive elements;
   (e) digitizing signals produced by the array in response to the first and second phase patterns for each pixel of the array; and
   (f) operating on the digitized signals to compute the relative height of each pixel of the surface.

* * * * *